United States Patent [19]

Lowe

[11] Patent Number: 4,987,910
[45] Date of Patent: Jan. 29, 1991

[54] TOOTH BRUSH DEVICE

[76] Inventor: Todd J. Lowe, 5600 Monmouth Ave., Ventnor, N.J. 08406

[21] Appl. No.: 438,054

[22] Filed: Nov. 20, 1989

[51] Int. Cl.⁵ ............................................ A45D 44/18
[52] U.S. Cl. ..................................... 132/309; 15/167.1
[58] Field of Search ................ 132/309, 311, 323, 324, 132/325, 326, 327, 328; 15/167.1

[56] References Cited

U.S. PATENT DOCUMENTS

| | | | |
|---|---|---|---|
| 301,055 | 6/1884 | Greene | 132/325 |
| 1,312,896 | 8/1919 | Donnelly | 132/309 |
| 1,427,857 | 9/1922 | Satterlee | 132/324 |
| 1,646,082 | 10/1927 | Dailey | 132/309 |
| 1,661,472 | 3/1928 | Gilbert | 132/324 |
| 1,666,877 | 4/1928 | Cummer | 132/324 |
| 1,792,429 | 2/1931 | Klinger | 132/309 |
| 1,813,360 | 7/1931 | Priest | 132/309 |
| 1,847,495 | 3/1932 | Priest | 132/309 |
| 2,113,439 | 4/1938 | Bean | 132/309 |
| 3,782,397 | 1/1974 | McCord | 132/309 |
| 3,830,247 | 8/1974 | Kaphalakos | 132/325 |
| 3,853,134 | 12/1974 | McCord | 132/309 |
| 3,939,853 | 2/1976 | Spanondis | 132/323 |
| 4,286,611 | 9/1981 | Talbot | 132/321 |
| 4,821,752 | 4/1989 | Widlak | 132/311 |

Primary Examiner—John J. Wilson
Assistant Examiner—F. LaViola, Jr.

[57] ABSTRACT

A tooth brush device comprising an elongated body having first and second end portions and an intermediate portion between the end portions, bristles at the first end portion of the body providing a brush while the second end portion provides a handle for the tooth brush device. The intermediate portion of the body has a chamber for receiving a spool of dental floss to be dispensed by the device through an opening extending within the second end portion, and the body includes a window for monitoring the presence of dental floss within the chamber of the body. The window of the body may also be provided by an opening to the chamber and a transparent window cover removably secured with the body enclosing the opening. The cover includes spool retaining structure which is received within the chamber for rotatably retaining within the chamber a spool of dental floss for the dispensing of floss by the device.

5 Claims, 1 Drawing Sheet

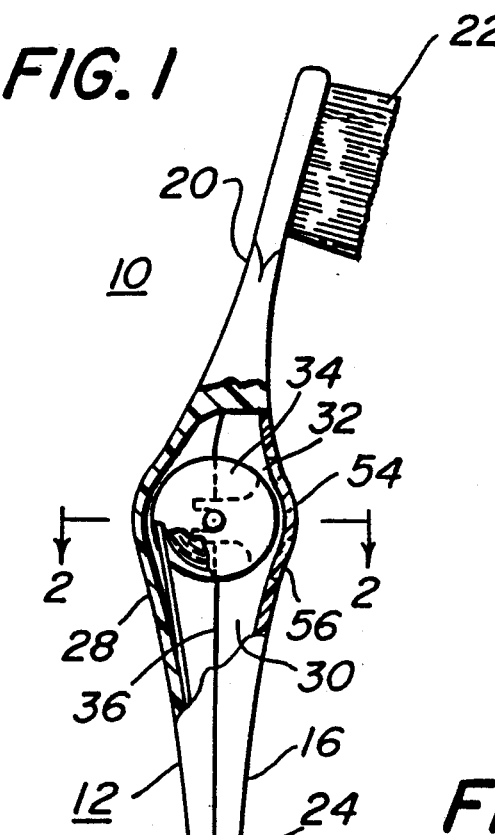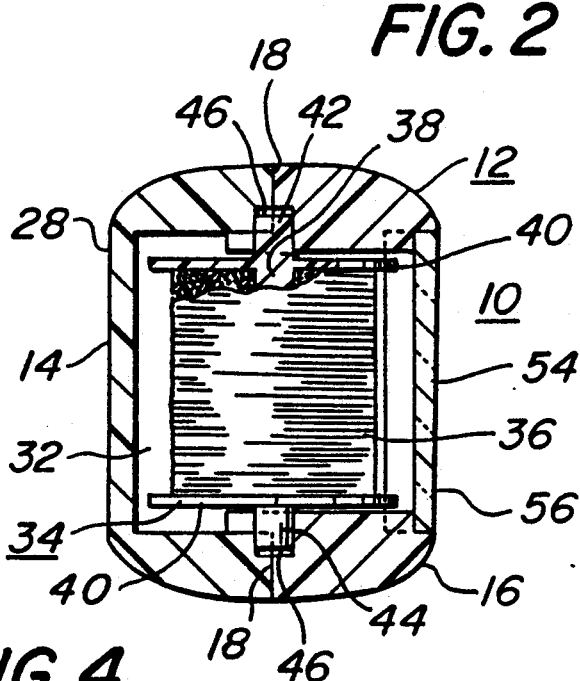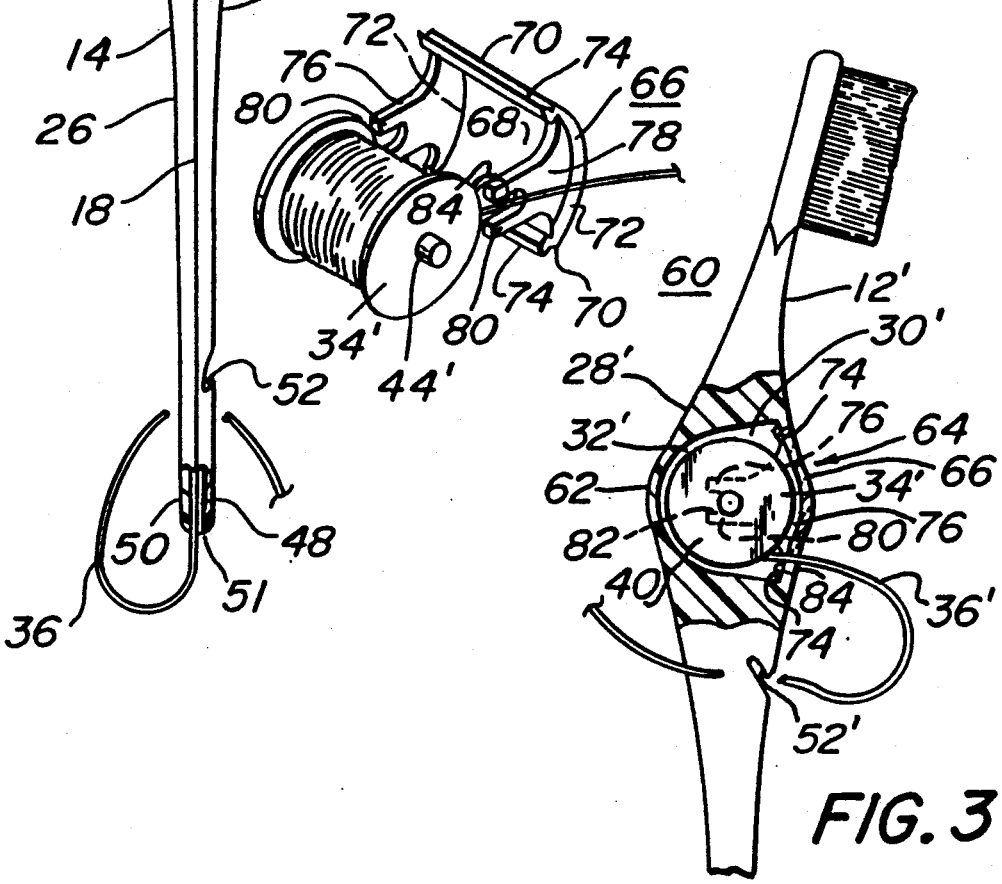

TOOTH BRUSH DEVICE

The invention relates to a tooth brush device, and more particularly to a tooth brush device including means for dispensing dental floss therefrom.

BACKGROUND OF THE INVENTION

Heretofore tooth brush devices have been provided for dispensing dental floss, such as the tooth brushes shown in U.S. Pat. Nos. 2,113,439 and 3,782,397. However, in such devices, in which the dental floss is retained on a spool within an enclosed chamber, the spool of floss is not visible and may be exhausted without warning to the user. To avoid this, it would be desirable for the user to know the remaining supply of dental floss, so that if the tooth brush device is disposable, another tooth brush device can be made available for use prior to exhaustion of floss. In the case where the tooth brush device is provided with a replaceable spool of dental floss, it is also desirable to monitor the usage of dental floss so that a new spool may be available when required for replacement.

SUMMARY OF THE INVENTION

It is, therefore a principal object of the invention to provide a new and improved tooth brush device which dispenses dental floss.

Another object of the invention is to provide a new and improved tooth brush device for dispensing dental floss and permitting the monitoring of the dental floss stored in the device.

Another object of the invention is to provide a new and improved tooth brush device for dispensing dental floss which device is disposable when the supply of dental floss is exhausted.

Another object of the invention is to provide a new and improved tooth brush device for dispensing dental floss which has a replaceable supply of dental floss.

Another object of the invention is to provide a new and improved tooth brush device for dispensing dental floss, and allowing the resupply of dental floss and also the monitoring of the supply of dental floss for determining when such resupply is required.

Another object of the invention is to provide a new and improved tooth brush device for dispensing dental floss which allows monitoring by viewing of dental floss for determining whether the tooth brush device requires replacement for a disposable device and resupply of floss for a reusable device.

Another object of the invention is to provide a new and improved tooth brush device for dispensing dental floss which is convenient to use and inexpensive to manufacture.

The above objects as well as many other objects and advantages of the invention are provided by a tooth brush device comprising an elongated body having first and second end portions and an intermediate portion between the end portions. Bristles are secured to the first end portion of the body to provide a brush while the second end portion provides a handle for the tooth brush device. The intermediate portion of the body is provided with an enclosed magazine for storing dental floss, means for dispensing dental floss from the magazine and means for monitoring the presence of dental floss within the magazine. The magazine for dental floss of the tooth brush device comprises a chamber within the intermediate portion of the body for receiving a spool of dental floss. The intermediate portion also provides a window for monitoring by viewing the dental floss within the chamber of the body. The means for dispensing floss from the spool within the chamber of the body is provided by an opening extending within the second end portion of the body through which the floss passes for being dispensed at the end of the second portion of the body. The chamber of the body is configured to receive a spool of cylindrical form having floss wound thereabout. The spool has extending axle portions for rotatably engaging retaining means within the chamber and being rotatable for dispensing dental floss. The body of the tooth brush device may be of a plastic material with the intermediate portion proximate to the chamber having a transparent portion for providing the window for viewing the presence of dental floss on the spool within the chamber of the body. The second end portion of the body may be provided with a floss severing means for cutting floss dispensed by the tooth brush device.

In other form, the tooth brush device is provided with a window in its intermediate portion comprising a window opening to the chamber and a transparent window cover secured with the body over and enclosing the window opening. The cover of the window is removable to provide a passageway through the window opening for placing and replacing a spool of floss in the chamber of the body for being dispensed by the device. The intermediate portion of the body has an outer cylindrical surface with the window opening being in the outer cylindrical surface, while the window cover includes a transparent cylindrical portion removably received within the window opening and conforming with the cylindrical surface of the intermediate portion. The window cover also includes a pair of spool retaining elements extending from the cylindrical portion for being received within the chamber of the body and engaging and positioning a spool of dental floss within the chamber. The retaining elements of the window cover include means for engaging opposite sides of a spool of dental floss for rotatably supporting and positioning same within the chamber of the body. A cut out portion is provided in the window cover for communicating with the chamber and providing the means for dispensing therethrough floss which is stored within the chamber. The second end portion of the body may also be provided with a floss severing means proximate to the window opening for cutting floss dispensed by the tooth brush device.

DESCRIPTION OF THE DRAWING

The foregoing and other object of the invention will become more apparent as the following detailed description of the invention is read in conjunction with the drawing, in which:

FIG. 1 is a side elevational view with portions in section of a tooth brush device embodying the invention, FIG. 2 is an enlarged sectional view on line 2—2 of FIG. 1, FIG. 3 is a modified form of the tooth brush device of FIG. 1 having a portion in section and a portion broken away, and FIG. 4 is an enlarged perspective view showing the removable window cover of the tooth brush device and a spool of dental floss for being retained by the window cover when placed within the chamber of the tooth brush device.

Like reference numerals designated like parts throughout the several views.

DETAILED DESCRIPTION

Refer to FIGS. 1 and 2 which disclose a tooth brush device 10 including means for dispensing dental floss embodying the invention. The device 10 comprises a body 12 which for purpose of manufacture may be of a plastic material having first and second sections 14 and 16 which are joined together along mating surfaces represented by the line 18. The body 12 is elongated having a first end portion 20 to which bristles 22 are secured to provide a brush, and a second end portion 24 providing a handle 26. A central portion 28 of the body is intermediate the end portions 20 and 24 with the end portion 20 and 24 extending therefrom in substantially opposite directions.

The central portion 28 of the body 12 has an enlarged cross section while the handle 26 tapers to a reduced cross sectional size. The central portion 26 provides a chamber 30 therein forming a magazine for dental floss. The chamber has a cylindrically shaped cavity 32 for receiving therein a cylindrical spool 34. The spool 34 has dental floss 36 wound about its cylindrical core 38 and retained between its spaced sides 40. The core 38 of the spool 34 extends outwardly from each of the sides 40 to provide a pair of axle ends 42, 44. The axle ends 42, 44 are rotatably received within respective cylindrical depressions 46 formed between the first and second sections 14, 16 of the body at their mating surfaces 18 as shown in FIG. 2. In this manner, the spool 34 is retained in position within the chamber of the body, and is rotatable for dispensing dental floss 36. The end portion 24 has a passageway 48 extending therethrough from the chamber 30 to the outlet 51 its end 50. Dental floss 36 from the spool 34 extends through the passageway 48 and out of the outlet 51 and is dispensed by drawing the dental floss outwardly. As the dental loss 36 is dispensed, the spool 34 is caused to rotate with the withdrawal of floss. A length of dental floss 36 dispensed may be severed by the sharp edge provided by a cutting means 52 at the end 50 of the handle 26. The cutting means 52 which is provided by a slit in the handle 26 may also be used to retain the external end of the floss 36 by being wedged within the slit until such time as floss is again dispensed. The device 10 provides a window 54 for viewing the spool 34 retained within the chamber 30 and monitoring the floss 36 wound thereabout for determining the quantity of floss remaining on the spool. For this purpose, at least a portion of the body 12 proximate to the spool 34 is transparent to light as being provided with an opening or by a portion 56 of transparent material as shown in FIG. 2. Thus, the user of the tooth brush device 10 can monitor and determine when the device is about to have its floss fully dispensed while the floss is enclosed within the chamber 30 and protected from exposure and contamination. In this manner, the user could provide for the replacement of the tooth brush device with a new tooth brush device upon the disposal of the exhausted device, or the exhausted spool 34 can be replaced with a new spool of floss where the spool is replaceable.

The tooth brush device 60 illustrated by FIGS. 3 and 4 is a modified form of the device 10, and is similar to the device 10 so that only the differences will be described in detail. The body 12' of the tooth brush device 60 has a chamber 30' providing a cavity 32' of substantially cylindrical configuration for receiving therein a spool 34' with dental floss 36' wound thereon. The central portion 28' of the body 12' has an outer wall 62 which is substantially cylindrical in form as seen from the sectioned portion of FIG. 3. The wall 62 has a rectangular cut out region providing an opening or window 64 communicating with the cavity 32' and proximate to the spool 34' within the cavity 32'.

The window 64 is enclosed by a window cover 66 having a cylindrical window cover portion 68 (see FIG. 4) made of a transparent material conforming to the cylindrical form of the wall 62 of the central portion 28' of the body 12'. The window cover portion 68 is rectangular with opposite pairs of edges 70, 72 for fitting and being received into the rectangular cut out region of the window 64. The ends 70 of the window cover portion 68 each have a ledge 74 for being disposed under an edge of the opening or window 64 for retaining the window cover 66 in position within the opening 64. For placing the window cover 66 in position, the cover 66 may be of a resilient material allowing it to be flexed for its insertion into the window 64.

The window cover 66 is also provided with a pair of retaining portions 76 and 78 which extend parallel to each other from opposite sides 72 of the cover portion 68 and transverse to the cover portion 68. The ends 80 of each of the retaining portions 76 and 78 has a cut out portion or slot 82 (see FIG. 3) for receiving and rotatably retaining therein a respective one of the axles 44' of the spool 34' when the spool 34' is positioned within the cylindrical cavity 32' of the body 12'. For the purpose of dispensing floss 36' from the spool 34', the cover portion 68 of the cover 66 has a cut out portion or opening 84 which communicates with the cavity 32'. Thus, when the spool 34' of floss 36' is positioned for rotation within the chamber 30' by the retaining portions 80, floss 36' which passes from the spool 34' through the opening 84 may be easily withdrawn with the rotation of the spool 34'. The cutting means 52' which is located proximate to the dispensing opening 84 for floss 36' may be used to sever and retain the end of the floss 36' as described in connection with the tooth brush device 10.

The tooth brush device 60 allows observation of the supply of floss present on the spool through the window cover 68 while the floss is enclosed within the chamber 30' and protected from exposure and contamination as described in connection with the tooth brush device 10. In addition the tooth brush device allows the replacement of the spool 34' within the cavity 32' when the supply of floss is exhausted.

The tooth brush device also has a relatively slim configuration, is convenient to use and permits its handle which tapers to a reduced cross sectional size to be easily received through and within an opening of a tooth brush holder for being retained in the customary manner.

It will of course be understood that the description and drawing herein contained are illustrative merely, and that various modifications may be made in the structures disclosed without departing from the spirit of the invention.

What is claimed is:

1. A tooth brush device comprising an elongated body having a central portion and first and second portions extending in opposite directions therefrom, bristles secured with the first portion of the body providing a brush and the second portion providing a handle for the tooth brush device, the central portion of the body has a chamber therein for storage of dental floss, and the body includes means for dispensing dental floss stored in the chamber and a window for monitoring the floss stored in the chamber of the body, the window of the body comprises a window opening to the chamber and a transparent window cover secured to the body, over and enclosing the opening, the cover of the window is removable to provide a passageway through the window opening for placing and replacing a spool of floss within the chamber of the body for dispensing floss, the central portion of the body has an outer cylindrical surface with the window opening being in the outer cylindrical surface, and the window cover comprises a transparent cylindrical portion removably received and retained within the window opening and conforming with the outer cylindrical surface of the central portion, and the window cover includes a pair of projecting spool retaining elements extending from the cylindrical portion for being received within the chamber of the body for engaging and positioning a spool of dental floss received within the chamber.

2. The tooth brush device of claim 1 in which the retaining elements of the cover include means for engaging a spool of dental floss on opposite sides for rotatably supporting and positioning the spool within the chamber of the body.

3. The tooth brush device of claim 2 in which the window cover of the body has an opening for communicating with the chamber and providing the means for dispensing therethrough dental floss stored within the chamber.

4. The tooth brush device of claim 3 in which the central portion has an enlarged cross sectional size and its second portion tapers to a reduced cross sectional size as it extends from the central portion for providing a handle which can easily be received through and within an opening of a tooth brush retaining means.

5. The tooth brush device of claim 3 in which the second portion of the body is provided with a floss severing means for cutting floss dispensed by the tooth brush device.

* * * * *